United States Patent [19]

Greco

[11] 3,937,741

[45] Feb. 10, 1976

[54] PRODUCTION OF HYDROQUINONE

[75] Inventor: Nicholas P. Greco, Edgewood, Pa.

[73] Assignee: Koppers Company, Inc., Pittsburgh, Pa.

[22] Filed: Jan. 20, 1975

[21] Appl. No.: 542,605

Related U.S. Application Data

[63] Continuation-in-part of Ser. No. 267,534, June 29, 1972, Pat. No. 3,862,247, which is a continuation-in-part of Ser. No. 16,545, March 4, 1970, abandoned.

[52] U.S. Cl............ 260/621 M; 260/625; 204/74
[51] Int. Cl.²......................................... C07C 39/10
[58] Field of Search....... 260/621 M, 574, 575, 625, 260/621 H, 621 R; 204/74

[56] References Cited
UNITED STATES PATENTS

| | | | |
|---|---|---|---|
| 2,198,249 | 4/1940 | Henke et al. | 260/509 |
| 3,383,416 | 5/1968 | Benner | 260/575 |

Primary Examiner—James O. Thomas, Jr.
Assistant Examiner—W. B. Lone
Attorney, Agent, or Firm—Oscar B. Brumback; Herbert J. Zeh, Jr.

[57] ABSTRACT

Hydroquinone is made by electrolytically reducing nitrobenzene in an aqueous acid medium and thereafter maintaining the reaction medium containing the amino product, at a temperature of 200° to 300°C. for a sufficient time to hydrolyze the amino product to hydroquinone, and extracting the hydroquinone from the aqueous reaction medium.

6 Claims, No Drawings

PRODUCTION OF HYDROQUINONE

CROSS REFERENCE TO RELATED APPLICATIONS

In some aspects, this application is a continuation-in-part of my copending application Ser. No. 267,534, filed June 29, 1972 now U.S. Pat. No. 3,862,247 which, in turn, is a continuation-in-part of my application Ser. No. 16,545, filed Mar. 4, 1970 now abandoned.

BACKGROUND OF THE INVENTION

This invention relates to a process for the production of hydroquinone by the electrolytic reduction of nitrobenzene to amino products and the hydrolysis of the amino products to hydroquinone.

Hydroquinone has the characteristic of being easily oxidized to quinone and the quinone-like products. The principal large scale use of hydroquinone is as a photographic developer, but it is also used as a stabilizer and as an antioxidant for substances such as fats, oils, whole milk powders, vitamins, and the like.

Hydroquinone has been produced heretofore commercially by the oxidation of aniline in sulfuric acid with manganese dioxide or sodium dichromate to quinone and the reduction of the quinone with iron dust to hydroquinone. It has been suggested that hydroquinone can be produced by the electrolytic oxidation of benzene to quinone in the presence of sulfuric acid, using a lead anode and a lead cathode, and then the reduction of the quinone to hydroquinone. My copending application Ser. No. 267,534 describes the production of hydroquinone by the hydrolysis of para-aminophenol.

SUMMARY OF THE INVENTION

According to this invention hydroquinone is made from nitrobenzene by the electrolytic reduction of nitrobenzene in an aqueous acid medium to amino products; then hydrolyzing the amino products in the acid medium along with water to provide 40 to 120 moles of water per mole of nitrobenzene initially present by maintaining the aqueous reaction medium at a temperature of 200° to 300°C., preferably from 220° to 260°C., for a time sufficient to hydrolyze the hydrogenated product to hydroquinone; cooling the aqueous reaction medium; and extracting the hydroquinone from the cooled aqueous reaction medium with an organic water-immiscible solvent.

DETAILED DESCRIPTION

The starting material for use in the present invention is nitrobenzene. This starting material may be either of the two grades of nitrobenzene that are commercially available: Nitrobenzene (a technical undistilled product) and oil of mirbane (distilled nitrobenzene). The small amounts of hydrocarbons, both benzene and paraffins, and traces of m-dinitrobenzene, nitrophenol, and water that constitute the impurities in the technical grade do not appreciably affect the process. The oil of mirbane grade is quite pure, having a purity (by freezing point) better that 99.5%.

The sulfuric acid to be used should, of course, be electrolytic grade. Such grade can be obtained commercially at any strength between sp. gr. 1.200 (27.4%) and sp. gr. 1.835 (93.19%).

The reduction of the nitrobenzene to amino compounds which are precursors to hydroquinone is carried out in an aqueous sulfuric acid solution. The temperature should be maintained between 50° and 80°C. Any nitrobenzene remaining after the reduction, can be readily removed from the solution by steam distillation.

After the electrolytic reduction, the composition of the aqueous acid medium becomes important for the hydrolysis. The composition can be readily determined by analysis and adjusted as needed. The minimum requirement is that there be at least a mole of sulfuric acid per mole of nitrobenzene originally present in the reaction.

If mole ratio below 1 mole of sulfuric acid per mole of nitrobenzene originally present is used, insufficient conversion results and large amounts of unreacted starting materials remain in the aqueous solution. If mole ratio is above about 2 moles of sulfuric acid per mole of nitrobenzene originally present, the yield seems to drop.

Water must be present in an amount sufficient to provide for hydrolysis and also to act as solvent for the salts of the hydroquinone precursors, hydroquinone, ammonium bisulfate, and the ammonium sulfate that are formed during the course of the reaction. As an example, at least 40 moles of water per mole of nitrobenzene originally charged must be present to dissolve sufficient quantities of the reactants and products. More water up to about 120 moles may be used but excess water raises the practical problem of water removal for the recovery of the ammonium sulfate.

The temperature for the hydrolysis can vary over a wide range of from about 200° to 300°C. If temperatures below about 200°C. are used, an unduly long reaction time is required and the yields are not generally good. As the temperature is increased, the pressure must be correspondingly increased to maintain the reaction medium in the aqueous phase. At temperatures as high as 300°C., a steam pressure of up to about 1250 psig is required to maintain an aqueous phase and there is danger of resin formation if the contact time is too long. No advantage is obtained by increasing or decreasing the pressure to a value other than that which is sufficient to maintain a liquid phase. To avoid the use of considerable pressure, with the corresponding equipment requirements, temperatures in the range of 220° to 260°C. are preferred.

The reaction time or residence time of the reactants during hydrolysis varies with the temperature and to a lesser extent with the mole ratio of the reactants. At minimum temperature, e.g., 200°C., a per pass reaction time of 8 hours is ordinarily required. At 220°C., effective results from the standpoint of yield are obtained using a two-pass hydrolysis reaction and a reaction time of 3 hours per pass. At 220°C., satisfactory results can be obtained in a single pass hydrolysis step if the reaction time is extended to 7 or 8 hours. Hydrolysis can occur at temperatures above 250°C. in 5 minutes to a half hour. From a practical standpoint, the overall time per pass for hydrolysis can be considered to be from 5 minutes to 8 hours.

The hydrolysis can be carried out in one step or it can be carried out in two or more steps. It can be continued sequentially by terminating the reaction, cooling, extracting the hydrolysis product and reheating the hydrolysis mixture without further addition of reactants. While a one-step hydrolysis is desirable from the standpoint of ease and efficiency of operation, an increase in yield can usually be achieved by a second hydrolysis of the reation mixture after the product of the first hydrolysis has been extracted.

After the period of hydrolysis, the length of time of which is dependent to some extent on whether a single or multiple pass hydrolysis is used, the reaction mixture is cooled. Cooling is required to prevent resinification of the product in the acidic aqueous reaction mixture and to enable the separation of the by-product by organic solvent extraction. Any substantially water-immiscible solvent which will dissolve the product hydroquinone is useful. The preferred solvent is ethyl ether.

In the extraction, the organic solvent phase is then separated from the reaction mixture by decantation and the product is removed from the solvent by distillation or other means. Distillation provides a high purity hydroquinone as a product.

After removal of the hydroquinone, the resulting aqueous effluent reaction mixture can be reheated to the hydrolysis temperature for a second or even a third hydrolysis step. The second and subsequent hydrolysis steps are carried out as before; i.e., by heating the reaction mixture to the appropriate temperature of hydrolysis for the desired period of time, cooling and removing the hydroquinone product by solvent extraction.

The apparatus for the electrolytic reduction of the nitrobenzene may be a circular glass or glass-lined vessel with a porous cup separating the vessel into a anolyte chamber and a catholyte chamber. The anode is platinum and the cathode is carbon. Both electrodes are provided with binding posts for connection to the electric circuit. A stirrer is provided in the catholyte chamber. Heating and cooling coils are provided for the vessel.

The hydrolysis of the amino products can be carried in a Pfaudler kettle, with the higher temperatures of the hydrolysis, corrosion resistant construction materials become necessary. At temperatures up to 220° to 230°C., teflon reactors are effective. Higher temperature ranges require the use of more durable equipment such as tantalum-lined reactors.

Without further elaboration, it is believed that one skilled in the art can, by following the preceding description, utilize the present invention to its fullest extent. The following specific embodiment is, therefore, to be construed as merely illustrative, and not limitative of the disclosure.

A porous Alundum cup was secured in the center of a substantially larger glass vessel equipped with heating and cooling walls and a stirrer, the cup extending almost to the bottom of the vessel. The anode, constituted of a series of platinum wires, was placed inside the cup. The cathode, constituted of a series of carbon plates, was placed in the space between the sidewalls of the vessel and the cup. Thus the volume within the cup is the anolyte chamber and the annular space between the cup and the vessel is the catholyte chamber. An anolyte solution consisting of 100 grams of a 75% sulfuric acid solution is charged to the anolyte chamber. A catholyte solution consisting of 20 grams of nitrobenzene in 100 grams of 80% sulfuric acid was charged to the catholyte chamber. The vessel was maintained at a temperature of 50° to 80°C. To the electrodes was connected a direct current energy source capable of operating at 6 volts. Electricity was applied to the electrodes at the rate of 6 amperes per hundred square centimeters of electrode for a period of 3½ hours to reduce the nitrobenzene to amino products. During this time, a mechanical stirrer was operated in the catholyte chamber to direct the liquid in a downwardly direction in the catholyte chamber. At the end of this period the solution was removed from the catholyte chamber, diluted with 152 grams of water and 11 grams of ammonia gas was bubbled into the mixture to partially neutralize the sulfuric acid. Analysis of an aliquot showed about 16.8 grams of para-aminophenol to be present. The solution was then placed in a tantalum lined reactor and heated under pressure to a temperature of 240°C. and maintained at this temperature for 4 hours to hydrolyze the amino products to hydroquinone. The solution was cooled to room temperature and filtered to remove any solids. The filtrate was subjected to two extractions, each comprised of 200 milliliter portions of ethyl ether. The ether extracts were combined and evaporated to dryness. There remained 14.8 grams of crude hydroquinone. After purification by flash distillation under vacuum at 203°C./60 mm., there was obtained 12.8 grams of pure hydroquinone. This gave an overall yield based upon the nitrobenzene originally charged of 71.5%.

What is claimed is:

1. A process for the manufacture of hydroquinone from nitrobenzene which compreses the steps of:
    a. subjecting a solution of nitrobenzene in an aqueous sulfuric acid electrolyte at a temperature of 50° to 80°C to electrolytic reduction, thereby forming amino products,
    b. subjecting said electrolyte containing said amino products to hydrolysis at a temperature of 200° to 300°C for a period of time sufficient to hydrolyze said amino products to hydroquinone,
    c. cooling said hydrolysis solution, and
    d. extracting hydroquinone from said solution with a water immiscible organic solvent.

2. The process of claim 1 wherein said electrolytic reduction is carried out using a platinum anode and a carbon cathode.

3. The process of claim 1 wherein said water immiscible organic solvent is ethyl ether.

4. The process of claim 1 wherein the electrolytic reduction is carried out in a catholyte solution comprising 20 parts of nitrobenzene in 100 parts of sulfuric acid and in an anolyte solution comprising aqueous sulfuric acid having a concentration of 75% $H_2SO_4$.

5. The process of claim 1 wherein said hydrolysis is carried out with the ratio of reactants being at least one mole of sulfuric acid and 40 to 120 moles of water per mole of nitrobenzene originally subjected to said electrolytic reduction.

6. A process for the manufacture of hydroquinone from nitrobenzene which comprises the steps of:
    a. electrolytically reducing a solution of nitrobenzene in an aqueous sulfuric acid electrolyte at a temperature of 50° to 80°C. by passing a direct current through a circuit including a platinum anode and a carbon cathode to form amino products from said nitrobenzene,
    b. hydrolyzing said amino products by maintaining said solution at a temperature of 200° to 300°C. for a period of time ranging from 5 minutes to 8 hours and adjusting the composition of said solution to a ratio of at least 1 mole of acid and 40 moles of water per mole of nitrobenzene originally present whereby said amino products are hydrolyzed to hydroquinone, c. cooling said solution, and
d. extracting said hydroquinone from such solution with a water-immiscible organic solvent.

* * * * *